US009298730B2

(12) United States Patent
Colaco et al.

(10) Patent No.: US 9,298,730 B2
(45) Date of Patent: Mar. 29, 2016

(54) SYSTEM AND METHOD FOR VIEWING MEDICAL IMAGES

(75) Inventors: Vernon Colaco, Mission Viejo, CA (US); Vittorio Accomazzi, Ontario (CA)

(73) Assignee: International Medical Solutions, Inc., Mississauga (CA)

( * ) Notice: Subject to any disclaimer, the term of this patent is extended or adjusted under 35 U.S.C. 154(b) by 161 days.

(21) Appl. No.: 13/541,719

(22) Filed: Jul. 4, 2012

(65) Prior Publication Data

US 2014/0010421 A1  Jan. 9, 2014

(51) Int. Cl.
G06K 9/00 (2006.01)
G06F 17/30 (2006.01)
G06F 19/00 (2011.01)

(52) U.S. Cl.
CPC ........ G06F 17/30194 (2013.01); G06F 19/321 (2013.01)

(58) Field of Classification Search
None
See application file for complete search history.

(56) References Cited

U.S. PATENT DOCUMENTS

| 6,182,127 | B1 | 1/2001 | Cronin, III et al. |
| 6,262,749 | B1* | 7/2001 | Finger ................. G01S 7/52023 128/916 |
| 6,658,462 | B1 | 12/2003 | Dutta |
| 2002/0016718 | A1 | 2/2002 | Rothschild et al. |
| 2003/0217116 | A1 | 11/2003 | Currans |
| 2005/0054921 | A1* | 3/2005 | Katsman et al. ............ 600/437 |
| 2007/0124410 | A1* | 5/2007 | Hofstetter .................. 709/217 |
| 2008/0021740 | A1* | 1/2008 | Beane et al. .................. 705/3 |
| 2009/0103789 | A1* | 4/2009 | Danner ................. G06F 19/321 382/128 |
| 2009/0112882 | A1 | 4/2009 | Maresh et al. |
| 2009/0132285 | A1* | 5/2009 | Jakobovits ...................... 705/3 |
| 2010/0010983 | A1 | 1/2010 | Crucs |
| 2010/0011087 | A1* | 1/2010 | Hofsetter et al. ............ 709/217 |
| 2010/0138446 | A1* | 6/2010 | Canessa et al. .............. 707/770 |
| 2011/0093293 | A1* | 4/2011 | G. N. et al. ...................... 705/3 |
| 2011/0110568 | A1 | 5/2011 | Vesper et al. |
| 2011/0238618 | A1* | 9/2011 | Valdiserri et al. ............ 707/608 |
| 2012/0096524 | A1 | 4/2012 | Kovalan |
| 2012/0099769 | A1* | 4/2012 | Eichhorn ..................... 382/128 |
| 2012/0250956 | A1* | 10/2012 | Bocirnea ..................... 382/128 |
| 2012/0250990 | A1* | 10/2012 | Bocirnea ..................... 382/166 |

(Continued)

FOREIGN PATENT DOCUMENTS

EP    1217556 A2    6/2002

OTHER PUBLICATIONS

Dandu Ravi Varma, "Managing DICOM images: Tips and tricks for the radiologist", Indian Journal of Radiology and Imaging, DOI: 10.40103/0971-3026.95396, Jan. 2012, pp. 1-12.*

(Continued)

Primary Examiner — Bhavesh Mehta
Assistant Examiner — Oneal R Mistry
(74) Attorney, Agent, or Firm — Vito A. Canuso, III

(57) ABSTRACT

A method facilitates viewing of DICOM medical images by providing a 16-bit DICOM image on a computer readable storage medium, text-converted metadata of the DICOM image and an html-compatible conversion of the DICOM pixel data on a computer readable storage medium. Pixel data of the DICOM image is converted by dividing the 16-bit image into two 8-bit color channels stored in an image referenced by a web page using a uniform resource locator. The two 8-bit color channels are later reassembled within a portable web browser according to instructions set forth in computer readable program code associated with the web page.

7 Claims, 2 Drawing Sheets

(56) References Cited

U.S. PATENT DOCUMENTS

2012/0323606 A1* 12/2012 Ananthasu-
                              bramaniam ......... G06F 19/3418
                                                           705/3
2013/0091026 A1   4/2013 Deng et al.
2013/0305138 A1* 11/2013 Gicovate ....................... 715/234

OTHER PUBLICATIONS

Desai et al ("Medical Image Transcoder for Telemedicine Based on Wireless Communication Devices", Electronics Computer Technology (ICECT), 2011 3rd International Conference on (vol. 1), IEEE, Apr. 2011.*

Roentgen Works (Brit Systems, Browser-based DICOM Viewers, 2010.*

Lu et al (Oct. 2010): Research and Implementation of Converting DICOM Multi-Frame Medical Image to Multimedia Format 2010 International Conference on Multimedia Tech~zologyp. ages 1-5.

Desai et al (Apr. 2011): Medical image transcoder for telemedicine based on wireless communication devices. 3rd International Conference on Electronics Computer Technology. pp. 389-393.

Liu et al (Apr. 2007): Medical Image Conversion with DICOM. Canadian Conference on Electrical and Computer Engineering. pp. 36-39.

Teng (Aug. 2009): Managing DICOM iinage metadata with desktop operating systems native user interface. 22nd IEEE International Symposium on Computer-Based Medical Systems. pp. 1-5.

Lefebvre, International Search Report and Written Opinion of the Searching Authority, PCT/CA2013/001051, Dec. 17, 2013.

* cited by examiner

SYSTEM AND METHOD FOR VIEWING MEDICAL IMAGES

BACKGROUND OF THE INVENTION

The present invention relates generally to the field of image viewers. More particularly, the invention is related to image viewers for viewing medical images such as DICOM format images.

In the clinical practice it is very common to save patient's medical images to a media such as CD or DVD. This is usually done because the patient is required to be provided with a copy and images frequently need to be sent to a different institution.

Medical images are saved in DICOM format, which is not supported by the common operating systems such as Microsoft Windows™ or Apple Macintosh™. Therefore when the images are stored on the media it is very common to include an application to view them because, although DICOM is an international standard, not all DICOM viewers are equivalent. DICOM is a very large standard and not all viewers are capable of properly displaying every modality. For certain modalities some specific processing might be necessary for proper viewing. Therefore the presence of the viewer on the media, does not only guarantee the images can be properly viewed, but also guarantees that the images can be viewed correctly according to the modality of the provided image.

The technical challenge in creating a media viewer for viewing DICOM images that the viewer needs to run on every system, including very old systems, regardless of the memory, central processing unit or operating system. Furthermore, the viewer application should not rely on any user permission because the computer systems in hospitals typically have very tight security through which the user is not able to install any software nor make configuration changes. Thus the application should be capable of running directly from the media upon which the DICOM images are provided. For instance, currently, it is very common to require that a media viewer run on Windows XP™ operating systems released in 2001.

The current solution for medical imaging media viewer is to use antiquated applications, created contemporaneously with Windows XP™ released. These applications satisfy the minimal requirement and will run off the media. However, from a software engineering perspective, this approach has major drawbacks.

Old applications are difficult to maintain, extend and support. The tools necessary to develop them are frequently no longer available or supported. Extension in particular is a critical aspect, medical imaging modalities have changed since these viewers were released and they will continue to change.

In order to take advantage of new technologies, such as web viewing, companies are forced to create a second set of application independent from the media viewer. This requires duplicating the development effort in order to support both versions of a viewer.

SUMMARY OF THE INVENTION

According to one aspect of the present invention, a method for facilitated viewing of DICOM medical images is provided. The method comprises the steps of providing a 16-bit DICOM image on a computer readable storage medium; converting metadata of the DICOM image to text format; storing the text formatted metadata to a computer readable storage medium; and converting pixel data of the DICOM image to html compatible format.

Further objects of the invention include converting pixel data of the DICOM image to html compatible format by splitting the 16-bit DICOM image into two 8-bit channels; converting pixel data of the DICOM image to html format by losslessly compressing the two 8-bit channels using prig image format; loading the png image in an 'img' element; rendering the 'img' element in a html 5 canvas object; iterating through all pixel values of the canvas object to reconstruct the original 16-bit DICOM image; storing the html compatible formatted DICOM image to a computer readable storage medium and providing, to a web browser, DICOM image pixel data as offset from image beginning.

DETAILED DESCRIPTION OF THE INVENTION

Figure 1:
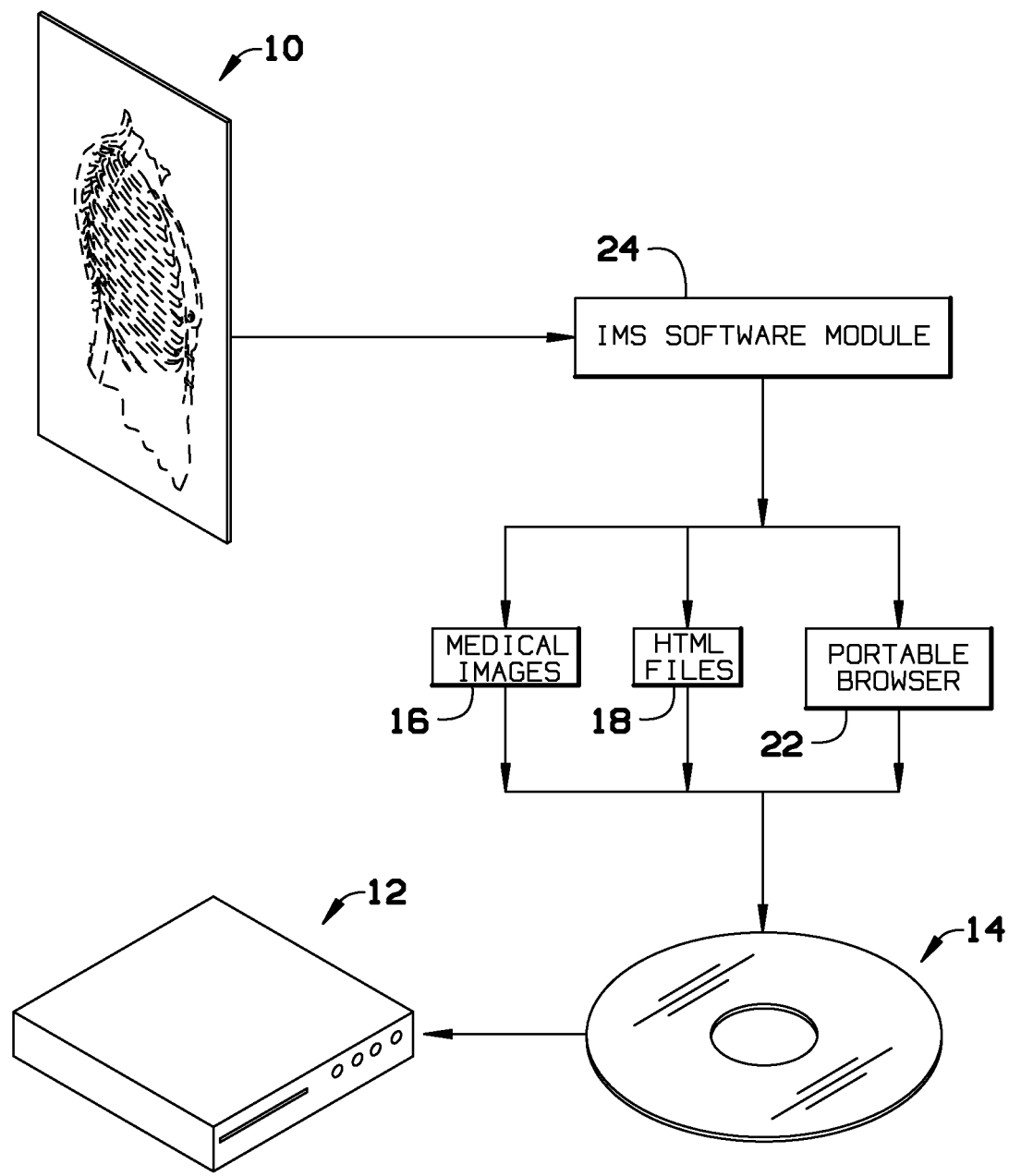
FIG. 1 illustrates a schematic view of a method of providing a portable media viewer according to a first exemplary embodiment of the present invention.

According to the preferred embodiment of the present invention, a media viewer packages a portable version of a html 5 capable browser on a computer readable medium to deliver the viewer as an html page.

A DICOM image contains meta information regarding the patient, medical modality, type and date of examination, etc. This meta information is stored in the DICOM image as key-value schema. Values may be of several types including string, integer and floating point or an array of these types. Keys and values are stored within DICOM images in binary form. Meta information needs to be provided to a user viewing the DICOM image.

In order to display the meta information, it is necessary to convert it. According to one embodiment of the present invention, the meta information is converted into a JSON data structure frequently used in JavaScript™ to store key-value pairs. Conversion includes parsing a binary stream of meta information using a DICOM library. During conversion, computer readable program code opens the DICOM image file and then loops through all tags for the key-value pairs of meta information to store the pairs in a JSON object as text values.

Exemplary code for converting DICOM metadata includes:

```
DicomFile df = newDicomFile(dicom_file_path)
    for each (Element tag in df.DataSet)
    {
        string tagKey = tag.Tag.ToString( );
        int tagMlt = tag.Vm;
        if (tagMlt > 0)
        {
            object tagVal = null;
            if (tagMlt > 1)
            {
                object [ ] arrVal = new object[tagMlt];
                for (int v = 0; v < tabMlt; v++)
                {
                    arrVal[v] = tag.Get(v);
                }
                tagVal = arrVal;
```

```
            }
            else
            {
                tagVal = tag.Get(0);
            }
            JSON.add(tagKey, tagVal);
        }
    }
```

Having parsed meta information from the DICOM image and saved into an object easily presented to a web browser, in order to provide the user with a version of the DICOM image that is viewable within a portable web browser 22, pixel data from the DICOM image must be converted into a web digestible format. The 16-bit gray scale DICOM image is converted into two color 8-bit images by splitting the 16-bits in two 8-bit channels such as red and green. Which color channel combination a developer uses is up to the individual developer. It is equally feasible to split the 16-bit grayscale image into the channels red and blue. Thus, for each pixel of the DICOM image, the 16-bit value is down-shifted to an 8-bit channel by effectively dividing by 256. This down-shifted result is stored as a first value. In this division, the remainder would otherwise be truncated resulting in a loss of information. To overcome this loss, a mask operator is used to collect the remainder value from the division and store as a second value. Each of the two stored values are subsequently associated with a web image channel which may be tagged by a url. Exemplary code for splitting the 16-bit grayscale image into two 8-bit color channels includes:

```
    for (int y = 0; y < nDicomImageColumns; y++)
    {
        for (int x = 0; x < nDicomImageColumns; x++)
        {
            ushort dicomGrayScale = DicomImage[x, y];
            byte valueH = ( byte)(dicomGrayScale >> 8 );
            byte valueL = (byte)(dicomGrayScale & 0xFF);
            WebImage[x,y].Red = valueL;
            WebImage[x,y].Green = valueH;
        }
    }
```

The resulting two-channel web image is next compressed using lossless compression such as the prig compression scheme. In some embodiments, implementation may be by Microsoft.NET using a standard Microsoft library. For this step, the pixel format BGR 24 is used.

The png image is then loaded in the html page by setting the source of the image element to the url containing the png image. Computer readable program code provided within the context of the url causes the png images to be loaded in an 'img' element having a tiled configuration of the two png channel images. This 'img' element is then rendered in an html 5 canvas object having the same size as the input image. Exemplary code for rendering the 'img' element includes:

```
        var tCanvas = document.createElement('canvas');
        tCanvas.width = img.width;
        tCanvas.height = img.height;
        tContext = tCanvas.getContext('2d');
        // draw img in canvas
        tContext.drawImage(img, 0, 0, img.width, img.height, 0,
0, img.width, img.height);
```

To extract the pixel data, and the computer readable program code causes an iteration through all the pixel values in the canvas element and reconstructs the original 16-bit value DICOM image. The green channel png is multiplied by 256 to produce a 16-bit value. The red channel pug is next added to the 16-bit value to yield the original DICOM image. Exemplary code for extracting the pixel data includes:

```
        var tBuffer = tContext.getImageData(0, 0, image.width,
           image.height);
        The pixel data element tBuffer is an array of 4 values for each
    pixel (red, green, blue and alpha).
        var pos = 0;
        var bData = tBuffer.data;
        var nPixels = img.width * img.height;
        for (var p = 0; p < nPixels; p++, pos += 4) {
        var val = bData[pos] + bData[pos + 1] * 256;
        pixels[p] = val;
```

The resulting extracted pixel data and the previously created JSON object may now be provided to a viewer using the portable browser provided on the media. As illustrated in FIG. 1, the original medical images 16, converted html-digestible files produced according to the method of the present invention and a portable browser 22 are supplied to a viewing party on a computer readable medium illustrated as a DVD or CD ROM 14 useable with a computer input device such as drive 12. Drive 12 interfaces with a central processing unit for providing data such as the converted html-digestible files from the computer readable medium to an output device such as a display or printer.

In the above-described approach, the original image date was converted into a second copy for html consumption. In a hybrid approach, data duplication may be avoided. DICOM image metadata is converted into a JSON object as described above. However, for pixel data conversion, an extra key-pair value is included in the metadata which stores the position of the pixel data in the DICOM image as offset from the beginning of the image. When the html page accesses the DICOM image, as byte stream. 16-bit values will be retrieved from each of the locations described in the extra key-value pair in the JSON object.

A binary reader uses AJAX call to retrieve the DICOM image as byte stream. Pixel is the array of the pixel retrieved.

The image is accessed using AJAX which is a standard technology allowing an html page to load information from a Web Server, or in the case of some browser, from local file system, in the background. Exemplary code to allow the web page to access the DICOM image includes:

```
        this.Start = function (ready) {
            var req = new XMLHttpRequest( );
            req.open('GET', url, true);
            req.onreadystatechange = function ( ) {
                if (req.readyState == 4) {
                    fileContents = req.responseText;
                    fileSize = fileContents.length;
                    if (ready != null) ready( );
                }
            }
            req.overrideMimeType('text/plain; charset=x-user-defined');
            req.send(null);
        }
```

The XMLHttpRequest object implements the AJAX call to retrieve the byte stream. The command overrideMimeType prevents the html page will from trying to interpret the data retrieved such that the data will be handled as a byte stream.

To subsequently retrieve the pixel data, the application retrieves the offset from the meta extra key-value pair provided within the JSON object of metal information and accesses the byte stream. Since the byte stream stores a list of 8-bit bytes, the 16-bit values can be computed by simply multiplying the high byte by 256 and adding the low bytes. Exemplary code to allow the web page to access the byte stream as 16-bit values includes:

```
var nPixels = width * height;
for (var p = 0; p < nPixels; p++) {
    var val = bReader.ReadByteAt(2 * p + offset) +
        bReader.ReadByteAt(2 * p + 1 + offset) * 256;
    pixels[p] = val;
}
```

Figure 2:
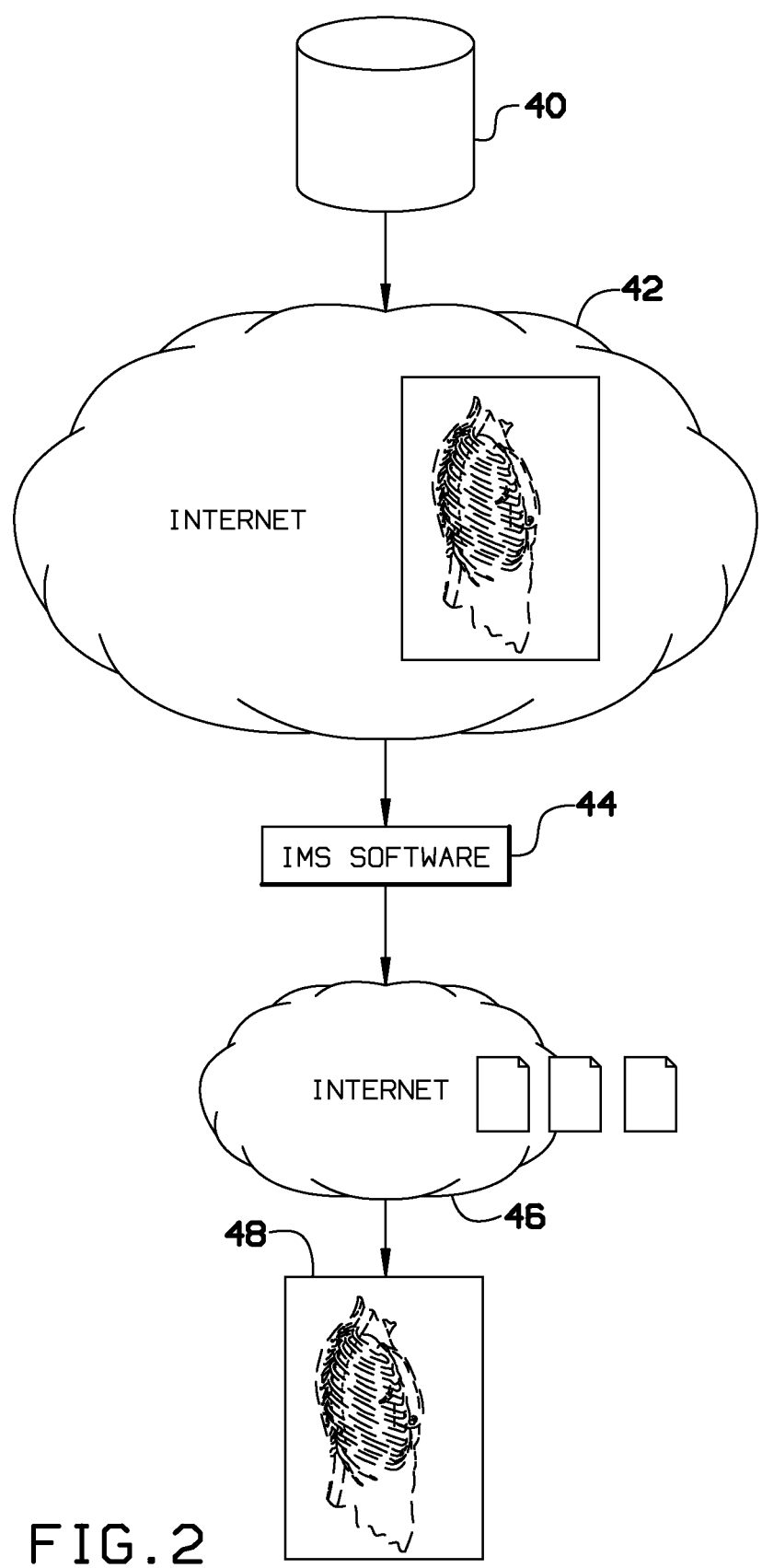
FIG. 2 illustrates a schematic view of a method of providing a portable media viewer according to a second exemplary embodiment of the present invention.

According to the schematic illustrated in FIG. 2, DICOM medical image data pertaining to a DICOM medical image to be viewed, may be sent from a database server 40 over a network including intranet 42 internet 46 or a combination of the two to a remote computing device for presentation to a display at 48 using the method described above. The computer readable program code 44 may be stored on a memory of a computer operably coupled to the database sewer, may be stored on a memory of the remote computing device or may be stored on a combination of the two or an intermediate computing device. Program code 44 may be referenced by a url within a browser processed on the remote computing device to facilitate asynchronous delivery of DICOM medical image data within the browser of the remote computing device without interfering with the display and behavior of an existing page displayed within the browser.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed is:

1. A method for facilitating the viewing of 16-bit images within DICOM files that contain meta data and 16-bit pixel data, the method configured to permit a portable browser to be used in order to view the 16-bit images, the method comprising:
    extracting from at least one DICOM file the meta data within the file;
    extracting pixel data offset information about where the 16-bit pixel data is stored in the DICOM file;
    storing onto a non-transitory computer-readable medium the meta-data and the pixel data storage information in an html-compatible format by storing a set of key-value pairs and then storing the entire set with JSON format on the medium;
    storing onto the non-transitory computer-readable medium the DICOM file;
    storing onto the non-transitory computer-readable medium an html page that contains instructions on how to read, using an html browser, the pixel data storage information and the 16-bit DICOM pixel data so as to maintain the full dynamic range of brightness and contrast of the original 16-bit image data, the instructions comprising computing the 16-bit image values by multiplying the high 8-bit byte by the number 256 to generate a result and then adding the low 8-bit byte to the result; and
    storing an html browser onto the non-transitory computer-readable medium;
    whereby a user desiring to view the 16-bit images from the DICOM file uses the browser to view the 16-bit images by having the browser read the meta data and perform the instructions for viewing the DICOM file in html.

2. The method of claim 1 further comprising extracting the 16-bit pixel data from the DICOM file and storing it onto the non-transitory computer-readable medium in an html-compatible format.

3. A method for facilitating the viewing of 16-bit images within DICOM files that contain meta data and 16-bit pixel data, the method configured to permit a portable browser to be used in order to view the 16-bit images, the method comprising:
    extracting the meta data from at least one DICOM file;
    extracting the 16-bit pixel data from the DICOM file;
    storing onto a non-transitory computer-readable the meta-data in JSON format and the 16-bit DICOM pixel data in its original uncompressed binary format without loss of any data so as to maintain the full dynamic range of brightness and contrast of the original data;
    storing onto the non-transitory computer-readable medium an html page that contains instructions on how to read, using an html browser, the 16-bit DICOM pixel data so as to maintain the full dynamic range of brightness and contrast of the original 16-bit image data, the instructions comprising computing the 16-bit image values by multiplying the high 8-bit byte by the number 256 to generate a result and adding the low 8-bit byte to the result; and
    storing an html browser onto the non-transitory computer-readable medium;
    whereby a user desiring to view the 16-bit images from the DICOM file uses the browser to view the 16-bit images by having the browser read the meta data and perform the instructions for viewing the DICOM file in html.

4. The method of claim 3, further comprising storing the 16-bit DICOM file onto the non-transitory computer-readable medium.

5. The method of claim 3 wherein the non-transitory computer-readable medium comprises a CD-ROM.

6. A method for using a browser to view 16-bit images within DICOM files to permit client-side rendering, the method comprising:
    accessing a non-transitory computer-readable medium comprising: (a) a DICOM file, (b) pixel data offset information about where the 16-bit pixel data is stored in the DICOM file, where the pixel data offset information is stored as a set of key-value pairs with JSON format; (c) an html browser; and (d) an html page that contains instructions on how to read, using an html browser, the pixel data storage information and the 16-bit DICOM pixel data so as to maintain the full dynamic range of brightness and contrast of the original 16-bit image data, where the instructions comprise computing 16-bit image values by multiplying the high 8-bit byte by the number 256 to generate a result and adding the low 8-bit byte to the result;
    opening the browser such that the browser can access the html page of instructions;
    using the browser to locate a 16-bit image from the byte stream in the DICOM file using the pixel data offset information; and computing 16-bit image values by multiplying the high 8-bit byte for the 16-bit image by the number 256 to generate a result and then adding low 8-bit byte to the result.

7. A method for using a browser to view 16-bit images within DICOM files to permit client-side rendering, the method comprising:

accessing a non-transitory computer-readable medium comprising: (a) 16-bit DICOM pixel data extracted from a DICOM file where the pixel data is stored in its original uncompressed binary format without loss of any data so as to maintain the full dynamic range of brightness and contrast of the original data; (b) an html browser; and (c) an html page that contains instructions on how to read, using an html browser, the 16-bit DICOM pixel data so as to maintain the full dynamic range of brightness and contrast of the original 16-bit image data, where the instructions comprise computing 16-bit image values by multiplying the high 8-bit byte by the number 256 to generate a result and adding the low 8-bit byte to the result;

opening the browser such that the browser can access the html page of instructions and the 16-bit DICOM pixel data; and computing 16-bit image values by multiplying the high 8-bit byte for the 16-bit image by the number 256 to generate a result and then adding the low 8-bit byte to the result.

* * * * *